United States Patent
Schipper et al.

(10) Patent No.: US 7,746,980 B1
(45) Date of Patent: Jun. 29, 2010

(54) X-RAY REFLECTOMETRY SYSTEM WITH MULTIPLE SAMPLE HOLDER AND INDIVIDUAL SAMPLE LIFTING MECHANISM

(75) Inventors: Rolf-Dieter Schipper, Karlsruhe (DE); Eduard Konusch, Bretten (DE); Rachel Eisenhower, Karlsruhe (DE); Lutz Bruegemann, Durmersheim (DE)

(73) Assignee: Bruker AXS GmbH, Karlsruhe (DE)

( * ) Notice: Subject to any disclaimer, the term of this patent is extended or adjusted under 35 U.S.C. 154(b) by 45 days.

(21) Appl. No.: 12/314,723

(22) Filed: Dec. 16, 2008

(51) Int. Cl.
*G01N 23/20* (2006.01)
*H05G 1/00* (2006.01)

(52) U.S. Cl. .............. 378/79; 378/70; 378/86; 378/208

(58) Field of Classification Search .............. 378/70, 378/79, 86, 208
See application file for complete search history.

(56) References Cited

U.S. PATENT DOCUMENTS

| | | | | |
|---|---|---|---|---|
| 3,527,942 | A * | 9/1970 | Roe et al. | 378/81 |
| 3,598,992 | A * | 8/1971 | Bridge, Jr. | 378/79 |
| 3,920,151 | A * | 11/1975 | Roe | 221/232 |
| 4,770,593 | A * | 9/1988 | Anderson | 414/222.08 |
| 5,257,302 | A * | 10/1993 | Narukawa | 378/45 |
| 6,111,930 | A * | 8/2000 | Schipper | 378/79 |
| 6,457,862 | B1 * | 10/2002 | Sumii et al. | 378/208 |
| 6,700,951 | B2 * | 3/2004 | Sumii | 378/44 |

OTHER PUBLICATIONS

Broshure, "D8 Discover" Bruker AXS GmbH, Karlsruhe, Germany, 2008.
Broshure, "XRD$^2$" Bruker AXS GmbH, Karlsruhe, Germany, 2008.
Broshure, "FABLINE", Bruker AXS GmbH, Karlsruhe, Germany, 2008.

* cited by examiner

*Primary Examiner*—Edward J Glick
*Assistant Examiner*—Thomas R Artman
(74) *Attorney, Agent, or Firm*—Paul Vincent

(57) ABSTRACT

An X-ray reflectometry apparatus comprises an X-ray source (1) configured to emit an incident X-ray beam directed onto a sample measuring position and an X-ray detector (2) configured to detect an X-ray beam (3) reflected from a surface of a selected sample (4) located in said sample measuring position and with a multiple sample holder (5) comprising an essentially horizontal one- or two-dimensional array of sample resting positions into which solid samples can be placed from above. A drive mechanism (6) moves the sample holder in one or two directions within a horizontal plane underneath the sample measuring position in order to place a selected sample (4) directly beneath the measuring position and a sample lift mechanism (7) has a vertically movable piston (8) located below the multiple sample holder (5) beneath the sample measuring position. When the sample lift mechanism (7) is activated, the piston (8) moves upwards against a bottom surface of the selected sample (4) or sample container (9) containing said selected sample (4), lifts the selected sample (4) or sample container (9) until it touches a stop (10) that keeps the sample (4) in the sample measuring position. When the sample lift mechanism (7) is deactivated, the piston (8) moves downwards and the sample (4) rests in its resting position. The device prevents signal cross talk to neighboring samples or to the sample holder, while also assuring an alignment which can be parallel to the incident beam.

7 Claims, 2 Drawing Sheets

ND SAMPLE HOLDER AND
X-RAY REFLECTOMETRY SYSTEM WITH MULTIPLE SAMPLE HOLDER AND INDIVIDUAL SAMPLE LIFTING MECHANISM

BACKGROUND OF THE INVENTION

The invention concerns an X-ray reflectometry apparatus comprising an X-ray source configured to emit an incident X-ray beam directed onto a sample measuring position and an X-ray detector configured to detect the X-ray beam following reflection from a surface of a selected sample located in that sample measuring position and with a multiple sample holder comprising an essentially horizontal one- or two-dimensional array of sample resting positions into which solid samples can be placed from an upward direction. A drive mechanism moves the sample holder in one or two directions within a horizontal plane beneath the sample measuring position in order to place a selected sample directly below the measuring position.

An X-ray system of prior art comprises an X-ray source and a detector unit. A sample (wafer) is positioned between the detector and the X-ray source and is disposed on an Euler's balance. A knife-edge is positioned above the sample and can be manually lowered towards the surface of the sample using a micrometer screw adjustment mechanism. An indicating caliper is utilized to measure the separation between the knife-edge and the surface of the sample. This apparatus is only suitable for reflectometry measurements in the middle region of the sample, since, in the event that the sample is moved in the x or y directions, the knife edge moves along therewith and causes blockage of the beam emanating from the X-ray source, since that source is stationary (see "D8 Discover" brochure, Bruker AXS GmbH, Karlsruhe, Germany, 2008).

A screening apparatus of prior art utilizes an X-ray source and a detector to examine a selected one of a plurality of samples disposed in a sample holder configured as a plate having 96 receptacles in which 96 samples can be placed. A knife-edge is located above the sample and is intended to prevent other samples from being illuminated, in particular, for small angles of incidence of the X-ray beam. Without the knife-edge, X-rays would be incident on a plurality of samples and the resulting scattering would significantly complicate signal analysis. The knife-edge is fixed in space and is aligned manually. The samples within the sample holder are moved in position in the x and y direction and measured individually. Reflectometry measurements are not possible using this apparatus, since the surface of individual samples may not be aligned with the surface of the surrounding sample holder or cannot be prepared to be flush with the surface of the sample holder. In the event that the surface of the sample is below the level of the sample holder, that surface is inaccessible to reflectometry measurements, since such measurements are typically made at angles within the range of 0 to 5 degrees relative to the horizontal. If the sample is excessively high, the angle of incidence is in error (see the brochure "XRD ²", Bruker AXS GmbH, Karlsruhe, Germany, 2008).

Another device of prior art proposes an X-ray analysis system, which is suitable for large volume, rapid series, automated measurement processes. Wafers can be examined with spatial resolution and each particular measuring point can be adjusted and aligned with respect to the X-ray beam in a highly automated manner. When a plurality of small wafers are to be measured sequentially while disposed within a common support, problems result due to the fact that not all the wavers have the same thickness. Measurements can also be distorted by thin layers which are deposited on the wafer surfaces. An upstream wafer may cast a shadow on a downstream wafer, thereby preventing initial measurements at an angle of approximately zero degrees, cause falsification of the reflectometry measurements, and/or generate unreliable data (see the brochure "FABLINE", Bruker AXS GmbH, Karlsruhe, Germany, 2008).

In view of these problems and difficulties regarding devices of prior art, it is the underlying purpose of the present invention to develop a system for X-ray reflectometry measurements on a plurality of samples which prevents signal cross-talk to neighboring samples or to the sample holder, while assuring an alignment which can be parallel to the incident beam.

SUMMARY OF THE INVENTION

The object of the invention is achieved by providing a sample lift mechanism having a vertically movable piston disposed below the multiple sample holder beneath the sample measuring position. Upon activation of the sample lift mechanism, the piston moves upwards against a bottom surface of the selected sample or sample container holding said selected sample to lift the selected sample or sample container until it touches a stop that keeps the sample in the sample measuring position. When the sample lift mechanism is deactivated, the piston moves downwards and the sample assumes its resting position.

Prior art measurements addressed the problem of contamination between neighboring samples or of scattering from the sample holder itself by limiting the measuring area to the area directly beneath the knife edge. Sample alignment was previously performed by moving the sample through the X-ray beam parallel to the sample surface, to determine where the incident beam intensity was reduced by 50 percent. In contrast thereto, and in accordance with the invention, the problem of contaminated reflectance is solved by placing only the sample to be measured in the X-ray beam, while leaving the sample holder with the other samples beneath the plane of measurement. Moving the sample to be measured against the stop positioned at the measuring height thereby solves the problem of alignment. Since the sample surface is moved to the proper height for measurement, the invention functions properly with samples of varying thickness.

In accordance with the invention, a mechanism is provided to lift the sample out of the sample holder and to move the selected sample against the sample stop. The sample stop provides sufficient contact with the sample for accurate positioning but nevertheless allows the incoming and reflected beams to pass through. A series of samples can thereby be investigated using X-ray reflectometry without any further time consuming sample-to-sample alignment with respect to the height and the tilt angle (z, and θ respectively). A sample library is thereby moved to position the first sample to be measured between the lift and the stop. The lift is beneath the sample and the stop is above the sample. Upon command from suitable measurement software, the lift rises up to a specific value. During this lifting motion, the lift contacts the underside of the sample and urges the top surface of the sample against the sample stop. The reflectometry measurement is then performed. After completion of the measurement, the lift moves back down, returning the sample to the sample library along the course of travel. This process of sample positioning, lifting, measuring and returning is repeated for all samples to be examined.

In a preferred embodiment of the invention, the system comprises a knife-edge located directly above the sample measuring position. This embodiment has the advantage that the knife-edge can easily be disposed, structured, and dimensioned to limit the measurement area on the selected sample surface.

In a preferred variation of the above embodiment, the knife-edge is vertically adjustable relative to the sample. This variation has the advantage of permitting straightforward adjustment of the area on the sample surface, which is to be irradiated by X-rays.

In a further preferred embodiment of the invention, the piston comprises a spring for pressing the sample or sample container against the stop. This embodiment has the advantage of defining the pressure with which the sample is urged against the stop to decrease or prevent the likelihood of damaging the stop or the sample in the event if inadvertent exercise of excess pressure.

In an additional preferred embodiment of the invention, the stop has a horizontal bottom plane defining a reference height for the sample measuring position and the samples or sample containers have corresponding flat top planes. This embodiment has the advantage of providing means for defining an exact vertical sample position as well as exact horizontal alignment of the selected sample surface when the sample or sample container is pressed against the stop.

In a preferred embodiment of the invention, the system comprises standardized sample containers configured to rest in openings in the sample holder at the sample resting positions, the openings having a larger cross-section in their upper parts that house the sample containers and smaller cross-sections in their lower parts that permit access of the piston to the bottoms of the sample containers. This embodiment has the advantage of providing secure seating of the samples while nevertheless permitting lifting of a selected sample by the piston into the measuring position.

Further preferred aspects of the invention can be extracted from the drawings. The features shown and described in association with the drawing are exemplary only and do not constitute an exhaustive enumeration of inventive elements. The features shown and described therein can be utilized in accordance with the invention individually or collectively in arbitrary combination.

DESCRIPTION OF THE PREFERRED EMBODIMENT

Figure 1:
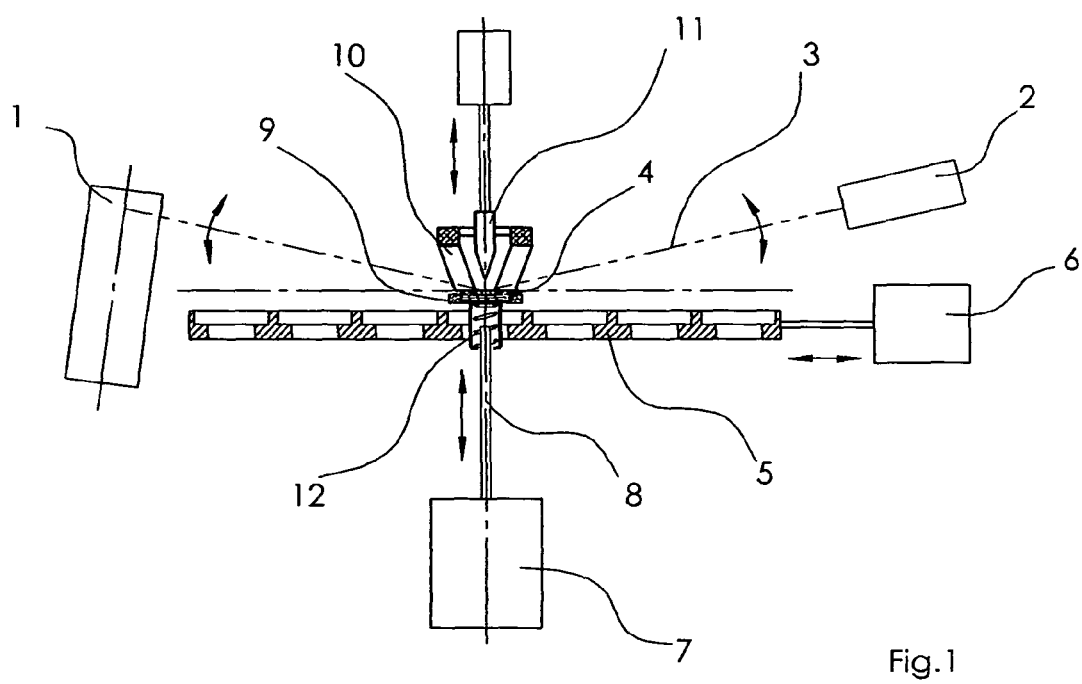
FIG. 1 shows a schematic side view of the X-ray reflectometry system in accordance with the invention in a position of the sample appropriate for measurement.

Referring to FIG. 1, the X-ray spectrometry system in accordance with the invention has an X-ray source 1 irradiating an X-ray beam 3 towards a sample 4. Following interaction with the sample 4, the X-ray beam is incident on a detector 2 positioned opposite to the X-ray source 1 with respect to the sample 4. Both the angle of the X-ray beam 3 emanating from the X-ray source 1 as well as the angle of detection of the X-ray detector 2 can be adjusted relative to the substantially horizontal upper surface of the sample 4, as is schematically indicated by the curved arrows proximate the X-ray source 1 and X-ray detector 2 in FIG. 1, respectively. A multiple sample holder 5 is situated below a surface of the sample 4 being measured. The multiple sample holder has a plurality of openings for accepting a large number of samples. The openings have a wider upper region and a narrower lower region. A drive mechanism 6 interacts with the multiple sample holder 5 to displace the multiple sample holder 5 in the x and y directions as indicated by the horizontal arrow proximate reference symbol 6 in FIG. 1. A sample lifting mechanism 7 is disposed below the sample and comprises a moveable piston 8 which can exercise an up and down motion as indicated by the vertical double arrow in FIG. 1 proximate reference symbol 8. The moveable piston 8 engages a bottom surface of a selected X-ray sample 4 to urge that sample up against a bottom surface of a stop mechanism 10. A spring configuration 12 cooperates with the end of the moveable piston 8 in such a fashion as to exercise a resilient spring force on the bottom portion of the sample 4 thereby providing controlled pressure between the upper surface of the sample 4 and the lower surface of the stop 10. Each sample 4 is positioned within a sample holder 9 and is dimensioned to seat within an upper opening of the multiple sample holder 5. As clearly seen in the figure, the upper opening of the multiple sample holder 5 accommodates the outer dimensions of the sample including a sample container. The narrower lower opening is sufficient to provide clearance for the moveable piston 8 to address the bottom side of the sample 4. The stop 10 is disposed appropriately above the sample holder and has a bottom surface engaging the upper surface of the sample 4. A knife-edge 11 is disposed within the stop 10 with a pointed side thereof facing downwards towards the sample 4. Adjustment of the distance between the pointed edge of the lower edge of the knife-edge 11 and the sample 4 selects the area of irradiation on the sample by the X-ray beam. The knife-edge 11 can be moved up and down in the vertical direction to change the distance between the lower edge of the knife-edge 11 and the upper surface of the sample as indicated by the double vertical arrows proximate the knife-edge 11 in FIG. 1.

Figure 2:
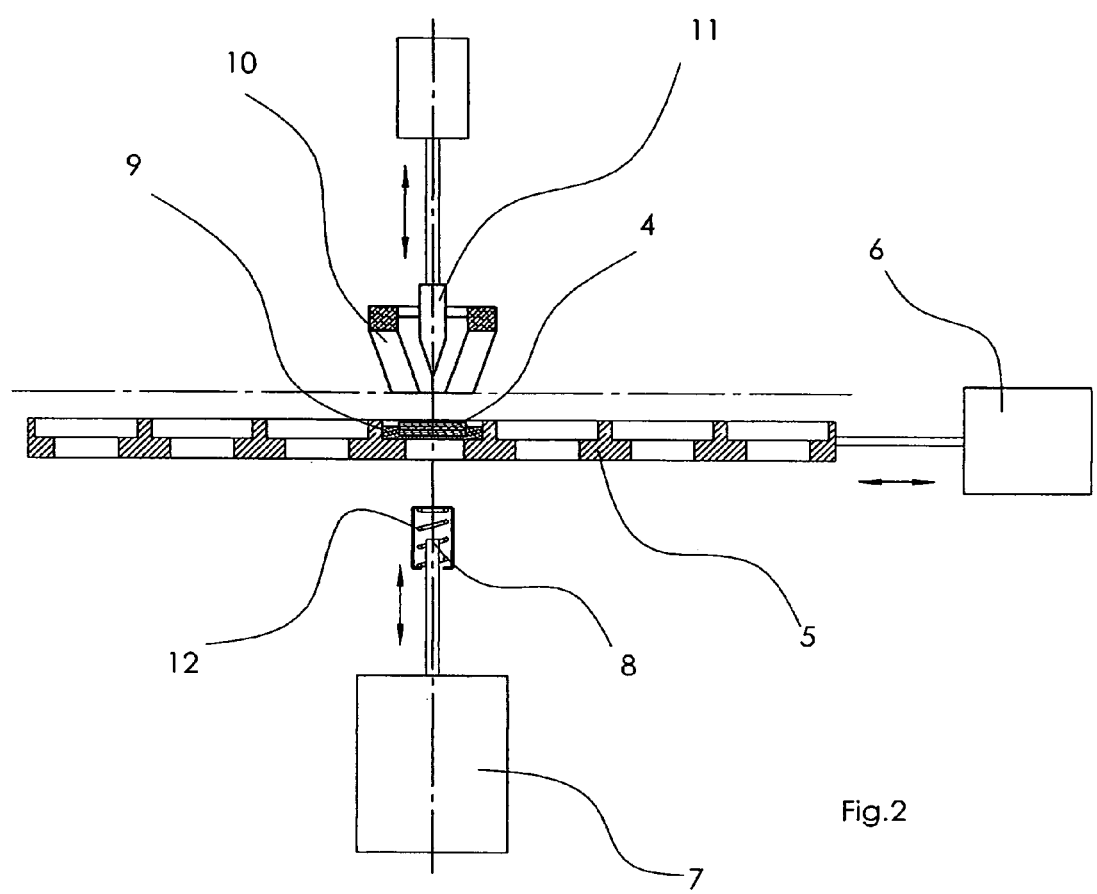
FIG. 2 shows a further view of the X-ray reflectometry system in accordance with FIG. 1, however, with the sample in a lowered position.

FIG. 2 shows an analogous view of the X-ray reflectometry system of FIG. 1, however, with the sample 4 seated in the upper opening of the holder 5 and within a sample holder 9. As can been seen from FIG. 2, the piston mechanism 8 has been retracted into the lifting mechanism 7 through vertical motion in accordance with the double arrows in the lower potion of the figure proximate reference symbol 7. The spring mechanism 12 moves down along with the moveable piston 8 and thereby lowers the sample 4 back into its neutral location out of the measurement position. Subsequent thereto, the drive mechanism 6 can be exercised to position the next sample 4 to be measured. For reasons of clarity, neither FIG. 1 nor FIG. 2 show the full possible complement of samples within the sample holder 5.

The apparatus functions in the following manner.

The samples 4 to be measured seat in the perforated tray 5 in a grid layout with regular, periodic spacings between the samples. The (x,y) coordinates of the samples to be measured are specified through the use of a graphical user interface. Lines in x or y, (x,y) grids or non-uniform (x,y) positions are possible. A suitable computer interface creates an appropriate job file, which includes the list of (x, y) coordinates of the sample positions of the samples to be measured. This job file also includes measurement conditions such as angular range, generator power and speed of measurement. The sample library 4 is moved such that the first sample 4 to be measured is positioned between the lift 7 and the stop 10. The lift 7 is beneath the sample 4 and the stop 10 is above the sample. On command from the measurement software, the lift 7 drives a piston 8 to a specified height. On its way up, the piston 8 contacts the underside of the sample 4 and pushes the sample's top surface against the sample stop 10. During job execution, there is a fixed distance between the sample stop 10 and the knife-edge 11. This fixed distance in turn determines the illuminated sample area during the reflectometry measurement. The reflectometry measurement is then performed according to the conditions specified in the job file. The piston 8 moves back down, returning the sample 4 to the sample library 5 along the way. This process of sample positioning, lifting, measuring and returning is repeated for all the samples 4 of the library which are to be measured.

LIST OF REFERENCE SYMBOLS

1 X-ray source
2 X-ray detector
3 X-ray beam
4 selected sample
5 multiple sample holder
6 drive mechanism to move the sample holder
7 sample lift mechanism
8 moveable piston
9 sample container
10 stop
11 knife-edge
12 spring

We claim:

1. An X-ray reflectometry apparatus for examination of a selected sample at a sample measuring position using an X-ray beam, the apparatus comprising:
    an X-ray source, said source configured to emit the X-ray beam for incidence on the selected sample at the sample measuring position;
    an X-ray detector configured to detect the X-ray beam following reflection from a surface of the selected sample located in the sample measuring position;
    a multiple sample holder having a substantially horizontal, one- or two-dimensional array of sample resting positions into which solid samples can be lowered;
    a drive mechanism to move said sample holder in one or two directions within a horizontal plane to place the selected sample directly beneath the sample measuring position;
    a stop disposed directly above the measuring position; and
    a sample lift mechanism disposed below said multiple sample holder beneath the sample measuring position, said sample lift mechanism having a vertically movable piston, wherein, upon activation of the sample lift mechanism, said piston moves upwards against a bottom surface of the selected sample and lifts the selected sample until it touches said stop to position and maintain the selected sample in the measuring position, and, upon deactivation of said sample lift mechanism, said piston moves downwards to move said sample into a resting position within said sample holder.

2. The apparatus of claim 1, further comprising a knife-edge disposed directly above the sample measuring position.

3. The apparatus of claim 2, wherein said knife-edge is vertically adjustable relative to the sample.

4. The apparatus of claim 1, wherein said piston comprises a spring for pressing the sample, or a sample container in which the sample is held, against said stop.

5. The apparatus of claim 1, wherein said stop has a defined horizontal bottom plane defining a reference height for the sample measuring position and the samples or sample containers holding the samples have corresponding flat top planes.

6. The apparatus of claim 1, further comprising standardized sample containers configured to rest in openings of said sample holder at sample resting positions, said holes having a larger cross-section in upper parts that house said sample containers and smaller cross-sections in lower parts that establish access of said piston to bottoms of said sample containers.

7. An X-ray reflectometry apparatus for examination of a selected sample at a sample measuring position using an X-ray beam, the apparatus comprising:
    an X-ray source, said source configured to emit the X-ray beam for incidence on the selected sample at the sample measuring position;
    an X-ray detector configured to detect the X-ray beam following reflection from a surface of the selected sample located in the sample measuring position;
    a multiple sample holder having a substantially horizontal, one- or two-dimensional array of sample resting positions into which solid samples can be lowered;
    a drive mechanism to move said sample holder in one or two directions within a horizontal plane to place the selected sample directly beneath the sample measuring position;
    a stop disposed directly above the measuring position, said stop having a defined horizontal bottom surface area defining a reference height for the sample measuring position, wherein the samples have corresponding flat top surface areas to define an exact vertical sample position as well as an exact horizontal alignment of the selected sample when it is pressed against said stop and said surfaces engage;
    a sample lift mechanism disposed below said multiple sample holder beneath the sample measuring position, said sample lift mechanism having a vertically movable piston, wherein, upon activation of the sample lift mechanism, said piston moves upwards against a bottom surface of the selected sample and lifts the selected sample until it touches said stop to position and maintain the selected sample in the measuring position, and, upon deactivation of said sample lift mechanism, said piston moves downwards to move said sample into a resting position within said sample holder;
    a spring cooperating with an upper end of said piston to press the sample against said stop with a defined pressure;
    a vertically adjustable knife edge disposed directly above the sample measuring position and configured to limit a measurement area on the selected sample; and
    standardized sample containers configured to rest in holes of said sample holder at sample resting positions, said holes having a larger cross-section in upper parts that house said sample containers and smaller cross-sections in lower parts that establish access for said piston to bottoms of said sample containers.

* * * * *